United States Patent [19]

Steinbrink et al.

[11] Patent Number: 4,918,161

[45] Date of Patent: Apr. 17, 1990

[54] LOW MOLECULAR WEIGHT PULMONARY SURFACTANT PROTEINS

[75] Inventors: D. Randall Steinbrink, Melrose; Joanna Floros; David S. Phelps, West Roxbury, all of Mass.; H. William Taeusch, Redondo Beach, Calif.

[73] Assignee: Genetics Institute, Inc., Cambridge, Mass.

[21] Appl. No.: 190,287

[22] Filed: May 4, 1988

Related U.S. Application Data

[63] Continuation-in-part of Ser. No. 100,372, Sep. 24, 1987, Ser. No. 897,183, Aug. 15, 1986, abandoned, and Ser. No. 781.130, Sep. 26, 1985, abandoned, said Ser. No. 100,372, is a continuation-in-part of Ser. No. 897,183, which is a continuation-in-part of Ser. No. 781,130.

[51] Int. Cl.$^4$ .................. C07K 13/00; A61K 37/02
[52] U.S. Cl. .................................... 530/300; 530/324
[58] Field of Search .............. 514/2, 21, 12; 530/300, 530/324, 325, 326, 327

[56] References Cited

U.S. PATENT DOCUMENTS 4,659,805  4/1987  Schilling, Jr. et al. ............. 530/350

Primary Examiner—John Kight
Assistant Examiner—Nathan M. Nutter
Attorney, Agent, or Firm—David L. Berstein; Bruce M. Eisen

[57] ABSTRACT

This invention relates to novel proteins useful for enhancing pulmonary surfactant activity, methods for obtaining said proteins and compositions containing one or more of the proteins.

4 Claims, No Drawings

LOW MOLECULAR WEIGHT PULMONARY SURFACTANT PROTEINS

This application is a continuation-in-part of U.S. Ser. Nos. 100,372 (filed Sept. 24, 1987 as a CIP of 897,183 and 781,130); 897,183 (filed Aug. 15, 1986 as a CIP of 781,130); and 781,130 (filed September 26, 1985), the contents of which are hereby incorporated by reference.

FIELD OF THE INVENTION

This invention relates to proteins originally isolated from human lung lavage, methods for obtaining said proteins and uses thereof.

BACKGROUND OF THE INVENTION

Throughout this application various publications are referenced. Full citations for these publications may be found at the end of the specification The disclosure of these publications are hereby incorporated by reference in order to more fully describe the state of the art to which this invention pertains.

Hyaline Membrane Disease (HMD) and Respiratory Distress Syndrome (RDS) are synonymous terms denoting the clinical condition of pulmonary dysfunction in premature infants. The disease is attributable to the absence of surface active material (surfactant) which lines the air-alveolar interface in the lung and prevents collapse of the alveoli during respiration. Current therapy is predominantly supportive. However, recent clinical trials indicate that one promising therapy is the instillation of bovine-derived surfactant into the lungs of the neonate.

Surface tension in the alveoli of the lung is lowered by a lipoprotein complex called pulmonary surfactant. This complex consists of phospholipid and 5-10% protein (King, 1982). The protein fraction of the surfactant is composed of nonserum and serum proteins. The major surfactant associated protein is reportedly a 35,000 dalton nonserum, sialoglycoprotein (Shelly et al., 1982; Bhattacharyya et al, 1975; Sueishin and Benson 1981; King et al, 1973, Katyal & Singh, 1981). This protein reportedly seems to be important for the normal function of the pulmonary surfactant (King et. al., 1983; Hawgood et.al., 1985). It is present in reduced amounts in amniotic fluid samples taken shortly before the birth of infants who subsequently develop respiratory distress syndrome (Katyal and Singh, 1984; Shelly et al., 1982; King et al., 1975). Recently the biosynthesis of a 35,000 dalton protein in normal human lung tissue was studied and in an in vitro translation reaction, proteins of 29 and 31 kDa were identified as the primary translation products (Floros et al., 1985). A 35kDa protein also accumulates in the lungs of patients with alveolar proteinosis (Battacharyya and Lynn, 1978, Battacharyya and Lynn, 1980a). This protein has the same electrophoretic mobility, immunological determinants and peptide mapping as the 35kDa protein from normal human bronchoalveolar lavage material (Phelps et al., 1984; Whitsett et al., 1985).

In addition to the above mentioned proteins, the presence in rat lungs of a number of lower molecular weight surfactant-associated proteins has recently been reported. See D. L. Wang, A. Chandler and A. B. Fisher, Fed. Proc. 44(4): 1024 (1985), Abstract No.3587 (ca. 9000 dalton rat protein) and S. Katyal and G. Singh, Fed. Proc. 44(6): 1890 (1985), Abstract No. 8639 (10,000–12,000 dalton rat protein).

Additionally, a Feb. 6, 1985 press release from California Biotechnology Inc. reports the cloning and "detailed manipulation" of "the gene encoding human lung surfactant protein." However, the press release does not characterize that protein or describe the "detailed manipulations." Two other reports of possible surfactant-related proteins have also been published recently, namely, J.A. Whitsett et al., 1986, Pediatr. Res. 20:460 and A. Takahashi et al., 1986, BBRC 135:527.

The present invention relates to a new group of proteins recovered and purified from lung lavage of patients with alveolar proteinosis; methods for obtaining the proteins; corresponding recombinant proteins; antibodies to the proteins (which may be obtained by conventional methods now that the proteins may be obtained in pure form) for use, e.g. in diagnostic products; compositions containing the novel proteins; and methods for using the compositions, e.g. in the treatment of infants afflicted with conditions such as Respiratory Distress Syndrome (RDS), as a drug delivery vehicle in the administration of other therapeutic materials to the lungs or other organs and in the treatment of adult RDS, which can occur during cardiopulmonary operations or in other situations when the lungs are filled with fluid and natural pulmonary surfactant production and/or function ceases.

SUMMARY OF THE INVENTION

This invention relates to novel purified forms of human proteins useful for enhancing pulmonary surfactant activity, methods for obtaining said proteins in purified form and compositions containing one or more of the proteins. The proteins of this invention include the following:

1. A purified protein, i.e. free or substantially free from other human proteins, characterized by:
   (a) solubility in 1-butanol at 4° C.;
   (b) substantial insolubility in 1-butanol at −20° C., i.e. permitting protein precipitation therefrom;
   (c) containing the peptide sequence FPIPLPY-WL--AL (where "-" represents a non-determined amino acid residue); and,
   (d) a predominant band having an apparent molecular weight (MW) of ~6 kd as determined by SDS-PAGE analysis.

The protein so defined may be obtained and purified from lung lavage of patients suffering from alveolar proteinosis or may be produced by recombinant means, both as described herein, and should be useful in providing or enhancing enhancing pulmonary surfactant activity. Accordingly, this invention encompasses both the purified natural material as well as recombinant versions thereof. The amino acid composition of the protein as purified from lavage material is shown in Table 3. As described elsewhere herein, the recombinant form of the protein is encoded for by the DNA sequence of Table 1 or by a DNA sequence capable, or capable but for the use of synonymous codons, of hybridizing thereto under stringent conditions. "Stringent conditions" as the phrase is used herein are hybridization conditions substantially equivalent to 65° C. in 5 X SSC (1 X SSC=150 mM NaCl/0.15M Na Citrate). Thus this invention also encompasses proteins which are at least about 90% homologous, and preferably at least about 95% homologous, to polypeptide sequences encoded by the DNA sequence of Table 1.

2. A purified protein, i.e. free or substantially free from other human proteins, characterized by:

(a) solubility in 1-butanol at −20° C.;

(b) a predominant band having an apparent MW of about 6 kd as determined by SDS-PAGE; and, (c) an amino acid composition substantially as set forth in Table 2.

This protein should also be useful in providing or enhancing enhancing pulmonary surfactant activity.

TABLE 1
DNA and Corresponding Protein Sequence of 6K Clone

```
10
GAATTCCGGT GCC ATG GCT GAG TCA CAC CTG CTG CTG CTG TGG CTG CTG
           ... MET Ala Glu Ser His CTG Leu Leu Leu Leu Trp Leu Leu
                                   28                43

58  CCC CTC TGT GGC TGT GGC GCC ACT GCC TCC TCA GCC
    Pro Leu Cys Gly Cys Gly Ala Thr Ala Ser Ser Ala
                        73                         88

TCC CTT GCC
    Ser Leu Ala
    103

118 GGC CCT CCT GAG TGG CAG TTC TTG CAG AGC TTG CAG
    Gly Pro Pro Glu Trp Gln Phe Leu Gln Ser Leu Gln
                        133                148

GAT CAG TGC
    Asp Gln Cys
    163

AGA
Arg

178 TGC CAT GGG GAA CAA CAG CAT CTA CTA GTC GGA ATG GGA
    Cys His Gly Glu Gln Gln His Leu Leu Val Gly MET Gly
                    193                   208

GAT GCC CTA
    Asp Ala Leu

223 CAA TGT GAG AGG CAG TGG AAG GTC CAT GAT GTC AAG GCC
    Gln Cys Glu Arg Gln Trp Lys Val His Asp Val Lys Ala
                    238                253

AAG GAG GCC
    Lys Glu Ala
    268

283 GAC TTT CTG CTT CAA ATC CAG AGG CTG GTC GCC TGC CCC
    Asp Phe Leu Leu Gln Ile Gln Arg Leu Val Ala Cys Pro
                    298                313

TGC AAC AAC CCC
    Cys Asn Asn Pro

328 TTG AAG CTG ATG CCC TCA CAA CAG CAA AAC CTT GTG TAC
    Leu Lys Leu MET Pro Ser Gln Gln Gln Asn Leu Val Tyr
                    343                    358 373

TAC TTC ATG
    Tyr Phe MET

388 GAC TGC CCC TAC AAA GGG AAC ACT GAG CAG CCA GAC ATC
    Asp Cys Pro Tyr Lys Gly Asn Thr Glu Gln Pro Asp Ile
                    403                418

CCA CTG CCT
    Pro Leu Pro
    433

448 TCC CCT CGG AAA TCA GAG ATG CGG GAC CAG CCA GAC GCC
    Ser Pro Arg Lys Ser Glu MET Arg Asp Gln Pro Asp Ala
                    463                    478

TTG GCC AAC
    Leu Ala Asn

493 CTG GTG AAA GCG CCA GGG TCA CCT GCG GAC GCC CTG CTC
    Leu Val Lys Ala Pro Gly Ser Pro Ala Asp Ala Leu Leu
                    508                523                538

TAC TGT GGG
    Tyr Cys Gly
    (AAG Lys)

553 GTG CTG CCC CAG GGG CAG CAG ATT CTC CCT CAG CCT ACA
    Val Leu Pro Gln Gly Gln Gln Ile Leu Pro Gln Pro Thr
                    568                583

TGC TGC TAT
    Cys Trp Tyr

598 GAT CTC TCC CTC ATG ATT TTC ATG MET ATG GAC CAC CAC TGC
    Asp Leu Ser Leu MET Ile Phe MET MET Asp His His Cys
                    613                628 643

CTA CTG
    Leu Leu

658 ATC AAG CAG ATG CCC CAA TTC CCC CCC CCC CTC AAG TAT
    Ile Lys Gln MET Pro Gln Phe Pro Pro Pro Leu Lys Tyr
                    673                    688

TGC GCT GTG
    Cys Ala Val
    703

GCA
    Ala
```

TABLE 1-continued

DNA and Corresponding Protein Sequence of 6K Clone

| | | | | | | 718 TGC Cys | CGC Arg | GTG Val | GTA Val | 733 CTG Leu | GTG Val | GCG Ala | GGC Gly | GGC Gly | 748 ATC Ile | TGC Cys | CAG Gln | TGC Cys |
|---|---|---|---|---|---|---|---|---|---|---|---|---|---|---|---|---|---|---|
| GTG Val | GCC Ala | 763 GCT Ala | CAG Gln | GTG Val | | TCC Ser | CGC Arg | GTC Val | ATC Ile | CTC Leu | CTG Leu | ACG Thr | ATG MET | CTG Leu | | AGC Ser | CGC Arg | CTG Leu |
| CTG Leu | | | GAG Glu | CGC Arg | | | | 778 GTC Val | | | | | | | | | | |
| CCC Pro | | | CTG Leu | 823 GTC Val | TGC Cys | CGC Arg | GTC Val | GTC Val | CTC Leu | CTG Leu | TCC Ser | ATG MET | GAC Asp | GGC Gly | GAC Asp | AGC Ser | 808 ATG MET | GGC Gly |
| | | | | | | | | | | 838 CTC Leu | TGC Cys | TCC Ser | ATG MET | CTG Leu | GAC Asp | CAC His | GCT Ala | CTG Leu |
| 868 CCA Pro | AGG Arg | | TCG Ser | CCG Pro | ACA Thr | GGA Gly | GAA Glu | TGG Trp | CGG Arg | CGA Arg | GAC Asp | TCT Ser | GAG Glu | TGC Cys | 853 GAT Asp | 913 CAC His | CTC Leu | TGC Cys |
| ATG MET | TCC Ser | | GTG Val | ACC Thr | TGT Cys | CAG Gln | GCC Ala | GGG Gly | AAC Asn | AGC Ser | AGC Ser | CAG Gln | GAG Glu | AGC Ser | GAC Asp | CCA Pro | CAG Gln | GGC Gly |
| | | | | 928 GTG Val | 988 TGT Cys | | | 943 GGG Gly | | 958 CAG Gln | 973 GCA Ala | | | | | | | |
| ATG MET | CTC Leu | | CAG Gln | CAG Gln | ACC Thr | GCC Ala | GTT Val | TCC Ser | TGG Trp | TGG Trp | GAC Asp | GAA Glu | AGG Arg | AAG Lys | AAG Lys | AAG Lys | CAA Gln | TTT Phe |
| | | 1033 GAG Glu | | | | | | | | 1003 CTG Leu | | | | | 1018 TGC Cys | | | |
| GTG Val | CTC Leu | | CAG Gln | CAC His | ACG Thr | CCC Pro | CCC Pro | CTG Leu | CTG Leu | TGG Trp | CTG Leu | CAG Gln | CCC Pro | CCC Pro | GGC Gly | TGG Trp | GAT Asp | GCC Ala |
| | | | | 1093 TGC Cys | | | | 1048 CAG Gln | | | 1063 GTG Val | | | | | | | |
| CAC His | ACC Thr | ATC Ile | CAC His | AGC Ser | CAG Gln | GCC Ala | GCC Ala | AAC Asn | GGG Gly | TCC Ser | GAC Asp | ATG MET | CCC Pro | ATG MET | AGC Ser | CCT Pro | CTC Leu | CAG Gln |
| 1138 TGT Cys | ACC Thr | | | | | | | 1108 GTG Val | | | | | | | 1123 TCC Ser | | | |
| 1153 GAC Asp | 1166 TGATGAGAAC | 1176 TCAGCTGTCC | 1186 AGCTGCAAAG | 1196 GAAAAGCCAA | | | | | | | | | | | | | | |
| 1206 GTGAGACGGG | 1216 CTCTGGGACC | 1226 ATGGTGACCA | 1236 GGCTCTTCCC | 1246 CTGCTCCCTG | 1256 GCCCTCGCCA | 1266 GCTGCCAGGC | | | | | | | | | | | | |
| 1276 TGAAAGAAG | 1286 CCTCAGCTCC | 1296 CACACCGCCC | 1306 TCCTCACCTC | 1316 CCTTCCTCGG | 1326 CAGTCACTTC | 1336 CACTGGTGGA | | | | | | | | | | | | |
| 1346 CCACGGGCCC | 1356 CCAGCCCTGT | 1366 GTCGGCCTTG | 1376 TCTGTCTCAG | 1386 CTCAACCACA | 1396 GTCTGACACC | 1406 AGAGCCCACT | | | | | | | | | | | | |
| 1416 TCCATCCTCT | 1426 CTGGTGTGAG | 1436 GCACAGCGAG | 1446 GGCAGCATCT | 1456 GGAGGAGCTC | 1466 TGCAGCCTCC | 1476 ACACCTACCA | | | | | | | | | | | | |
| 1486 CGACCTCCCA | 1496 GGGCTGGGCT | 1506 CAGGAAAAAC | 1516 CAGCCACTGC | 1526 TTTACAGGAC | 1536 AGGGGGTTGA | 1546 AGCTGAGCCC | | | | | | | | | | | | |

TABLE 1-continued

DNA and Corresponding Protein Sequence of 6K Clone

| | | | | | | |
|---|---|---|---|---|---|---|
| 1556 CGCCTCACAC | 1566 CCACCCCCAT | 1576 GCACTCAAAG | 1586 ATTGGATTTT | 1596 ACAGCTACTT | 1606 GCAATTCAAA | 1616 ATTCAGAAGA |
| 1626 ATAAAAATG | 1636 CGAACATACA | 1646 GAACTCTAAA | 1656 AGATAGACAT | 1666 CAGAAATTGT | 1676 TAAGTTAAGC | 1686 TTTTTCAAAA |
| 1696 AATCAGCAAT | 1706 TCCCCAGCGT | 1716 AGTCAAGGGT | 1726 GGACACTGCA | 1736 CGCTCTGGCA | 1746 TGATGGGATG | 1756 GCGACCGGGC |
| 1766 AAGCTTTCTT | 1776 CCTCGAGATG | 1786 CTCTGCTGCT | 1796 TGAGAGCTAT | 1806 TGCTTTGTTA | 1816 AGATATAAAA | 1826 AGGGGTTTCT |
| 1836 TTTTGTCTTT | 1846 CTGTAAGGTG | 1856 GACTTCCAGC | 1866 TTTTGATTGA | 1876 AAGTCCTAGG | 1886 GTGATTCTAT | 1896 TTCTGCTGTG |
| 1906 ATTTATCTGC | 1916 TGAAAGCTCA | 1926 GCTGGGGTTG | 1936 TGCAAGCTAG | 1946 GGACCCATTC | 1956 CTGTGTAATA | 1966 CAATGTCTGC |
| 1976 ACCAATGCTA | 1986 ATAAAGTCCT | 1996 ATTCTCTTTT | 2006 AAAAAAAAAA | 2016 AAAAAAAAAA | 2026 AACGGAATTC | |

Deduced protein sequence of 6Kd PSP protein is underlined

TABLES 2 & 3

Amino acid compositions of the cold butanol insoluble and soluble "6 kd" proteins, respectively

|  | TABLE 3 | TABLE 2 |
|---|---|---|
| Asp/Asn | 3.06 | 2.7 |
| Thr | 1.18 | 2.0 |
| Ser | 2.55 | 2.1 |
| Glu/Gln | 5.97 | 1.6 |
| Pro | 7.64 | 6.3 |
| Gly | 7.38 | 22.9 |
| Ala | 9.13 | 3.3 |
| Cys | 9.14 | 0.95 |
| Val | 10.13 | 5.5 |
| Met | 3.46 | 3.4 |
| Ile | 6.46 | 4.8 |
| Leu | 16.23 | 17.3 |
| Tyr | 2.31 | 3.3 |
| Phe | 1.55 | 6.3 |
| His | .34 | 2.9 |
| Lys | 1.62 | 3.6 |
| Arg | 7.88 | 1.94 |

(calculated based on Mw = 10,000 daltons: ave residue Mw = 110)

Both proteins are referred to herein as "6 kd" proteins for the sake of simplicity, although it should be appreciated that other minor bands believed to represent incompletely processed forms of the proteins (e.g. at ~12 kd and/or ~16-18 kd) are also observed upon SDS-PAGE analysis of the proteins.

DETAILED DESCRIPTION OF THE INVENTION

The proteins of this invention were obtained by subjecting pulmonary lavage material from an alveolar proteinosis patient to a combination of separation techniques followed by chromatographic purification. More specifically, the lavage material was centrifuged, and the protein-containing pellet so obtained was washed with buffer and extracted with a solvent such as 1-butanol to remove lipids and lipid associated proteins. The butanol extract was set aside and treated as described below.

The 1-butanol-insoluble material was then washed, redissolved in buffer and purified chromatographically. Two proteins were thus obtained which are characterized by a molecular weight of about 35 kd. Those proteins are described in greater detail in in Published International Application WO 86/02037.

Butanol-soluble proteins were obtained by cryoprecipitation. More specifically, storage of the 1-butanol extract at −20° C. yielded a precipitate which was purified chromatographically to yield a protein characterized by a predominant band having an apparent molecular weight of about 6 kd (as determined by SDS-PAGE) and the observed amino acid composition set forth in Table 3. A second 6 kd (as determined by SDS-PAGE) protein was obtained by concentrating the supernatant to dryness and purifying the residue chromatographically. The observed amino acid composition of the latter 6 kd protein is set forth in Table 2.

The two low molecular weight proteins of this invention differ significantly from each other with respect to amino acid composition, as well as from the protein described by Tanaka, Chem. Pharm. Bull. 311:4100 (1983). Additionally, the N-terminal peptide sequence of the cold butanol-insoluble 6 kd protein was determined (Table 4). As previously mentioned, for the sake of simplicity, both low molecular weight PSP proteins are referred to hereinafter as "6k" proteins based on the approximate apparent molecular weights of their predominant protein bands as determined by conventional SDS-PAGE. It should be understood, however, that the actual molecular weights of these protein bands are presumably in the range of ~5-~9 kilodaltons.

The fact that these proteins can now be obtained in pure form by the above-described methods made it possible for one to apply conventional methods to elucidate the amino acid composition and sequence of the proteins; to prepare oligonucleotide probes based on the elucidated peptide sequences; to identify genomic DNA or cDNA encoding the proteins by conventional means, e.g., via (a) hybridization of labeled oligonucleotide probes to DNA of an appropriate library (Jacobs et al., 1985), (b) expression cloning (Wong et al., 1985) and screening for surfactant enhancing activity or (c) immunoreactivity of the expressed protein with antibodies to the proteins or fragments thereof; and to produce corresponding recombinant proteins using the identified genomic DNA or cDNA and conventional expression technology i.e. by culturing genetically engineered host cells such as microbial, insect or mammalian host cells containing the DNA so identified, for instance, transformed with the DNA or with an expression vector containing the DNA.

By way of example, genes encoding the two 35 kd proteins were cloned as described in detail in WO 86/02037.

Additionally, oligonucleotide probes based on the N-terminal sequence of the cold butanol-insoluble 6K protein (See Table 40) were synthesized and were used to screen a cDNA library prepared from human lung mRNA (Toole et al., 1984) as described in greater detail in Example 2, below. Several clones which hybridized to the probes were identified. Based on hybridization intensity one clone was selected, subcloned into M13 and sequenced. Plasmid PSP6K-17-3 was constructed by inserting the cloned cDNA so identified as an EcoRI fragment into the EcoRI site of plasmid SP65 (D.A. Melton et al., 1984, Nucleic Acids Res., 12:7035-7056). No. ATCC 40245. The nucleotide sequence of the cloned cDNA insert is shown in Table 1.

TABLE 4

| 1 |  |  |  | 5 |  |  |  |  | 10 |  |  |  |
|---|---|---|---|---|---|---|---|---|---|---|---|---|
| F | P | I | P | L | P | Y | (—) | W | L | (—) | (—) | A | L |

(—) = Not determined (positions 8, 11 & 12 were unidentified)

As those skilled in the art will appreciate, the cDNA insert in pSp6K-17-3 contains an open reading frame encoding a protein having a molecular weight of over 40 kd. It is believed that the primary translation product is further processed, e.g., by Type II pneumocytes (Alveolar Type II cells), to yield the approximately 6K protein. It is contemplated that the cloned cDNA, portions thereof or sequences capable of hybridizing thereto under stringent conditions may be expressed in host cells or cell lines by conventional expression methods to produce "recombinant" proteins having surfactant or surfactant enhancing activity.

With respect to the cloned approximately 6K protein, this invention encompasses vectors containing a heterologous DNA sequence encoding the characteristic peptide sequence Ile through Cys corresponding to nucleotides A-656 through C57 of the sequence shown in Table 1, i.e., IKRIQAMIPK-GALAVAVAQVCRVVPLVAGGICQC. One such vector contains the nucleotide sequence
ATC AAG CGG ATC CAA GCC ATG ATT CCC
AAG GGT GCG CTA GCT GTG GCA GTG

GCC CAG GTG TGC CGC GTG GTA CCT
CTG GTG GCG GGC GGC ATC TGC CAG
TGC

Other vectors of this invention contain a heterologous DNA sequence encoding at least a portion of the characteristic peptide sequence substantially as depicted in the underlined peptide region of Table 6, i.e., FPIPL-PYCWLCRALIKRIQAMIPK-GALAVAVAQVCRVVPLVAGGICQCLAERYS-VILLDTLLGRML. One such vector contains the DNA sequence substantially as depicted in the underlined nucleotide sequence of Table 1, i.e., TTC CCC ATT CCT CTC CCC TAT TGC TGG
CTC TGC AGG GCT CTG ATC AAG CGG
ATC CAA GCC ATG ATT CCC AAG GGT
GCG CTA GCT GTG GCA GTG GCC CAG
GTG TGC CGC GTG GTA CCT CTG GTG
GCG GGC GGC ATC TGC CAG TGC CTG
GCT GAG CGC TAC TCC GTC ATC CTG
CTC GAC ACG CTG CTG GGC ATG CTG Another exemplary vector contains a heterologous DNA sequence, such as the nucleotide sequence depicted in Table 1, which encodes the full-length peptide sequence of Table 1. DNA inserts for such vectors which comprise a DNA sequence shorter than the full-length cDNA of PSP6K-17-3, depicted in Table 1, may be synthesized by known methods, e.g. using an automated DNA synthesizer, or may be prepared from the full-length cDNA sequence by conventional methods such as loop-out mutagenesis or cleavage with restriction enzymes and ligation. Vectors so prepared may be used to express the subject proteins by conventional means or may be used in the assembly of vectors with larger cDNA inserts. In the former case the vector will also contain a promoter to which the DNA insert is operatively linked and may additionally contain an amplifiable and/or selectable marker, all as is well known in the art.

The proteins of this invention may thus be produced by recovering and purifying the naturally-occuring proteins from human pulmonary lavage material as described herein. Alternatively, the corresponding "recombinant" proteins may be produced by expression of the DNA sequence encoding the desired protein by conventional expression methodology using microbial or insect or preferably, mammalian host cells. Suitable vectors as well as methods for inserting therein the desired DNA are well known in the art. Suitable host cells for transfection or transformation by such vectors and expression of the cDNA are also known in the art.

Mammalian cell expression vectors, for example, may be synthesized by techniques well known to those skilled in this art. The components of the vectors such as the bacterial replicons, selection genes, enhancers, promoters, and the like may be obtained from natural sources or synthesized by known procedures. See Kaufman, Proc. Natl. Acad. Sci. 82: 689–693 (1985).

Established cell lines, including transformed cell lines, are suitable as hosts. Normal diploid cells, cell strains derived from in vitro culture of primary tissue, as well as primary explants are also suitable. Candidate cells need not be genotypically deficient in the selection gene so long as the selection gene is dominantly acting.

The host cells preferably will be established mammalian cell lines. For stable integration of vector DNA into chromosomal DNA, and for subsequenct amplification of integrated vector DNA, both by conventional methods, CHO (Chinese hamster Ovary) cells are generally preferred. Alternatively, the vector DNA may include all or part of the bovine papilloma virus genome (Lusky et al., Cell, 36:391–401 (1984)) and be carried in cell lines such as C127 mouse cells as a stable episomal element. Other usable mammalian cell lines include HeLa, COS-1 monkey cells, mouse L-929 cells, 3T3 lines derived from Swiss, Balb-c or NIH mice, BHK or HaK hamster cell lines and the like. Cell lines derived from Alveolar Type II cells may be preferred in certain cases such as expression of the 6K protein (alone or with one or more other proteins of this invention) using the cDNA insert from PSP6K-13-7 or a fragment thereof.

Stable transformants then are screened for expression of the product by standard immunological or enzymatic assays. The presence of the DNA encoding the proteins may be detected by standard procedures such as Southern blotting. Transient expression of the DNA encoding the proteins during the several days after introduction of the expression vector DNA into suitable host cells such as COS-1 monkey cells is measured without selection by activity or immunological assay of the proteins in the culture medium.

In the case of bacterial expression, the DNA encoding the protein may be further modified to contain preferred codons for bacterial expression as is known in the art and preferably is operatively linked in-frame to a nucleotide sequence encoding a secretory leader polypeptide permittng bacterial secretion of the mature variant protein, also as is known in the art. The compounds expressed in mammalian, insect or microbial host cells may then be recovered, purified, and/or characterized with respect to physicochemical, biochemical and/or clinical parameters, all by known methods.

One or more of the proteins of this invention may be combined with a pharmaceutically acceptable fatty acid or lipid such as dipalmitoylphosphatidyl choline or with mixtures of such fatty acids or lipids which may be obtained from commercial sources or by conventional methods, or with natural surfactant lipids to provide a formulated pulmonary surfactant composition. Natural surfactant lipids may be extracted by known methods from lung lavage, e.g. bovine or human lung lavage. Typically the weight ratios of total lipids to total proteins in the composition will be about 20:1 to about 100:1. At the levels currently being tested in clinical trials, one dose of the surfactant composition corresponds to 1-2 mg of total protein and 98-99 mg. of total lipid.

It is contemplated that certain subcombinations of one or more of the proteins of this intention with one or more of the proteins described in WO 86/02037 and compositions containing such subcombinations may be especially useful in the treatment of patients with particular clinical indications.

EXPERIMENTAL EXAMPLES

EXAMPLE 1

Isolation and Characterization of the Associated Proteins

Pulmonary lavage (50 ml) from an alveolar proteinosis patient was centrifuged at 10,000 ×g for 5 min. The pellet was collected and washed 5 times in 20 mm Tris HCl, 0.5 M NaCl, pH 7.4. The lipids and lipid-associated proteins were extracted from the washed pellet by shaking with 50 ml 1-butanol for 1 hr at room temperature.

The butanol extract so obtained Was stored at -20° C. causing precipitation of one of the low MW proteins. The precipitate was collected by centrifugation and dried under vacuum. The butanol layer containing butanol-soluble protein was evaporated to dryness. The precipitated cold butanol insoluble protein and the cold butanol-soluble protein were then purified in parallel by the same method as follows. Each crude protein was separately dissolved in CHC13 : MeOH (2:1, v/v), applied to Sephadex LH20 columns and eluted with CHC13:MeOH (2:1). The proteins were then analyzed by SDS-PAGE. Fractions containing the protein were pooled and evaporated to dryness. Amino acid composition was determined by hydrolysis in 6 N HCl at 110° C. for 22 hrs followed by chromatography on a Beckman model 63000 amino acid analyzer. N-terminal sequence was determined on an Applied Biosystems 470A sequencer. Molecular weights were determined on 10–20% gradient SDS polyacrylamide gels.

EXAMPLE 2

Screening of the cDNA Library and Sequencing of Clones for the 6Kd Proteins

Based on the first six amino acids of the sequence shown in Table 4 an oligonucleotide probe was synthesized. The probe consisted of six pools of 17 mers. Three of the pools each contained 128 different sequences, and three of the pools each contained 64 different sequences.Based on the first seven amino acids two pools of 20 mers were synthesized. These pools contained either 384 or 192 different sequences.

A cDNA library from human lung mRNA was prepared as described in Toole et al., (1984) and screened with the total mixture of the six pools using tetramethylammoniumchloride as a hybridization solvent (Jacobs et al., 1985). Approximately 100,000 phage were screened, and 100 phage which hybridized to the probe were plaque purified. The phage were then pooled into groups of 25 and screened with the individual 17 mer and 20 mer pools. Six phage which hybridized most intensely to one of the 20 mer oligonucleotide probes and one of the corresponding 17 mer pools (pool 1447 containing 128 different sequences) were plaque purified. The 17 mer pool 1447 was divided into four pools of 32 different sequences and hybridized to a dot blot of DNA prepared from these phage.

Based on the hybridization intensity, DNA from one of these six phage were subcloned into M13 for DNA sequence analysis. A sequence corresponding in identity and position to the amino acids shown in Table 4 was obtained, confirming that the isolated clone coded for the approximately 6kd cold butanol-insoluble protein found in the lavage material of alveolar proteinosis patients (see above).

The first clone obtained was presumed to be an incomplete copy of the mRNA because it lacked an initiating methionine, and was used to isolate longer clones. Two clones were completely sequenced by generating an ordered set of deletions with Bal 31 nuclease, recloning into other M13 vectors and sequencing via the dideoxynucleotide chain termination procedure (Viera and Messing, 1982; Sanger et al., 1977). One clone corresponded to a full-length copy of the type referred to as 17 (Table 1), the second began at nucleotide 148 of clone 17. Sequence of the 5'end of a third clone confirmed the sequence of the 5'end of clone 17. The clones are identical throughout the coding region and differ only at two positions in the 3'untranslated region.

As those of ordinary skill in this art will appreciate, the cloned gene may be conveniently obtained by excision from PSP6K-17-3 (ATCC No. 40245) or may be recloned using sequence information provided herein in Table 1.

REFERENCES

1. Bhattacharyya, S.N., and Lynn, W.S. (1978) Biochem. Biophys. Acta 537, 329–335
2. Bhattacharyya, S.N., and Lynn, W. S. (1980) Biochem. Biophys. Acta 625, 451–458
3. Bhattacharyya, S.N., Passero, M.A., DiAugustine, R.P., and Lynn, W. S. (1975) J Clin. Invest. 55, 914–920
4. Floros, J., Phelps, D.S., and Taeusch, W.H. (1985) J. Biol. Chem. 260, 495–500
5. Hawgood, S., Benson, B. J., and Hamilton, Jr. R. L. (1985) Biochemistry 24, 184–190
6. Hunkapiller, M. W. and Hood, L. E. (1983) Methods in Enzymology 91, 486–
7. Jacobs, K., Shoemaker, C., Rudersdorf, R., Neil, S. D., Kaufman, R. J., Mufson, A., Seehra, J., Jones, S. S., Hewick, R., Fritsch,E. E., Kawakita, M., Shimizu, T., and Miyake, T. (1985) Nature (Lond.) 313, 806–810.
8. Kafatos, E., Jones, W. C., and Efstratiadis, A. (1979) Nucleic acid Rest. 7, 1541–1552.
9. Katyal, S. L., Amenta, J. S., Singh, G., and Silverman, J. A. (1984) Am. J. Obstet. Gynecol. 148, 48–53.
10. Katyal, S. L. and Singh, G. (1981) Biochem. Biophys. Acta 670, 323–331.
11. King, R. J., Carmichael, M. C., and Horowitz, P.M. (1983) J. Biol. Chem. 258, 10672–10680.
12. King, R. J. (1982) J. Appl. Physiol. Exercise Physiol. 53, 1–8.
13. King. R. J., Klass, D. J., Gikas, E. G., and Clements, J. A. (1973) Am. J. Physiol. 224, 788–795.
14. King, R. J., Ruch, J., Gikas, E. G., Platzker, A. C. G., and Creasy, R. K. (1975) J. of Applied Phys. 39, 735–741.
15. Laemmli, U. K. (1970) Nature (Lond.) 227, 680–685.
16. Miller, J. S., Paterson, B. M., Ricciardi, R. P., Cohen, L and Roberts, B. E. (1983) Methods in Enzymology 101p. 650–674.
17. Phelps, D. S., Taeusch, W. H., Benson, B., and Hawgood, S. (1984) Biochem. Biophs. Acta, 791-22-6–238
18. Shelley, S. A., Balis, J. U., Paciga, J. E., Knuppel, R. A., Ruffolo, E. H., and Bouis, P. J. (1982) Am. J. Obstet. Gynecol 144, 224–228.
19. Sigrist, H., Sigrist-Nelson, K., and Gither, G. (1977) BBRC 74, 178, 184.
20. Sueishi, K., and Benson, G. J. (1981) Biochem. Biophys. Acta 665, 442–453
21. Toole, J. J., Knopf, J. L., Wozney, J. M., Sultzman L. A., Bucker, J. L., Pittman, D. D., Kaufman, R. J., Brown, E., Shoemaker, C., Orr, E. C., Amphlett, G. W., Foster, W. G., Coe, M. L., Knutson, G. L., Eass, D. N., Hewick, R. M. (1984) Nature (Lond.) 312, 342–347.
22. Whitsett, J A., Hull, W., Ross, G., and Weaver, T. (1985) Pediatric Res. 19, 501–508 23. Wong, G. G. et al., 1985, Science, 228:810–815

What is claimed is:

1. A purified human protein, free or substantially free from other human proteins, which is characterized by:

(a) solubility in 1-butanol at 4° C.;
(b) insolubility in 1-butanol at −20°C.;
(c) containing the peptide sequence FPIPLPY; and,
(d) a predominant band having an apparent molecular weight of ∼6 kiloDaltons by SDS-PAGE analysis.

2. A pulmonary surfactant composition comprising an effective surfactant enhancing amount of the protein of claim 1 and a pharmaceutically acceptable fatty acid and/or lipid.

3. A purified human protein, free or substantially free from other human proteins, which is characterized by:
(a) solubility in 1-butanol at 4° C.;
(b) solubility in 1-butanol at −20° C.;
(c) an amino acid composition substantially as
(d) a predominant band having an apparent molecular weight of ∼6 kilodaltons by SDS-PAGE analysis.

4. A pulmonary surfactant composition comprising an effective surfactant enhancing amount of the protein of claim 3 and a pharmaceutically acceptable fatty acid and/or lipid.

* * * * *